(12) United States Patent
Fielden et al.

(10) Patent No.: US 10,722,137 B2
(45) Date of Patent: Jul. 28, 2020

(54) SYSTEMS AND METHODS FOR ACCELERATED MR THERMOMETRY

(71) Applicants: University of Virginia Patent Foundation, Charlottesville, VA (US); The Board of Trustees of the Leland Stanford Junior University, Stanford, CA (US)

(72) Inventors: Samuel Fielden, Charlottesville, VA (US); Li Zhao, Charlottesville, VA (US); Wilson Miller, Charlottesville, VA (US); Xue Feng, Charlottesville, VA (US); Max Wintermark, Charlottesville, VA (US); Kim Butts Pauly, Charlottesville, VA (US); Craig H. Meyer, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 429 days.

(21) Appl. No.: 14/677,915

(22) Filed: Apr. 2, 2015

(65) Prior Publication Data
US 2015/0282733 A1 Oct. 8, 2015

Related U.S. Application Data

(60) Provisional application No. 61/974,234, filed on Apr. 2, 2014.

(51) Int. Cl.
| | |
|---|---|
| *A61B 5/055* | (2006.01) |
| *A61N 7/02* | (2006.01) |
| *A61B 5/01* | (2006.01) |
| *A61B 5/00* | (2006.01) |

(Continued)

(52) U.S. Cl.
CPC .............. *A61B 5/055* (2013.01); *A61B 5/015* (2013.01); *A61B 5/725* (2013.01); *A61N 7/02* (2013.01); *A61B 2018/00791* (2013.01); *A61B 2090/374* (2016.02)

(58) Field of Classification Search
CPC .... A61B 2018/00791; A61B 2090/374; A61B 5/015; A61B 5/055; A61B 5/725; A61N 7/02
See application file for complete search history.

(56) References Cited

U.S. PATENT DOCUMENTS

| | | | | |
|---|---|---|---|---|
| 2013/0307536 | A1* | 11/2013 | Feng ................. | G01R 33/5608 324/309 |
| 2015/0287222 | A1* | 10/2015 | Zhao ................. | G01R 33/5619 382/131 |
| 2015/0316630 | A1* | 11/2015 | Zhao ................. | G01R 33/4818 324/309 |

OTHER PUBLICATIONS

Lee et al. "Fast 3D Imaging Using Variable-Density Spiral Trajectories With Applications to Limb Perfusion" Magnetic Resonance in Medicine 50: 1276-1285 (2003).*

(Continued)

*Primary Examiner* — Michael T Rozanski
(74) *Attorney, Agent, or Firm* — Meunier Carlin & Curfman LLC (57) ABSTRACT

Aspects of the present disclosure relate to magnetic resonance thermometry. In one embodiment, a method includes acquiring undersampled magnetic resonance data associated with an area of interest of a subject receiving focused ultrasound treatment, and reconstructing images corresponding to the area of interest based on the acquired magnetic resonance data, where the reconstructing uses Kalman filtering.

12 Claims, 6 Drawing Sheets
(2 of 6 Drawing Sheet(s) Filed in Color)

(51) Int. Cl.
　　　*A61B 18/00*　　　(2006.01)
　　　*A61B 90/00*　　　(2016.01)

(56) References Cited

OTHER PUBLICATIONS

De Senneville, B.D. et al., "Kalman Filtering for undersampeled continuous volumetric MR-Temperature Imaging," Proc. Intl. Soc. Mag. Reson. Med., 2012, pp. 1558, 20.

Feng, X. et al., "Kalman Filter Techniques for Accelerated Cartesian Dynamic Cardiac Imaging," Magn Reson Med., 2013, pp. 1346-1356, 69(5), Wiley Periodicals, Inc.

Ishihara, Y. et al., "A Precise and Fast Temperature Mapping Using Water Proton Chemical Shift," Magn Reson Med., 1995, pp. 814-823, 34(6), Wiley-Liss, Inc.

Kennedy, J.E., "High-intensity focused ultrasound in the treatment of solid tumors," Nat Rev Cancer, 2005, pp. 321-327, 5(4).

Medel, R. et al., "Magnetic Resonance Guided Focused Ultrasound Surgery: Part 2: A Review of Current and Future Applications," Neurosurgery, 2012, pp. 755-763, 71(4).

Stafford, R.J. et al., "Monitoring of high-intensity focused ultrasound-induced temperature changes in vitro using an interleaved spiral acquisition," 2000, Magn Reson Med., pp. 909-912, 43(6), Wiley-Liss, Inc.

Todd, N. et al., "Reconstruction of fully 3-D high spatial and temporal resolution MR temperature maps for retrospective applications," Magn Reson Med., 2012, pp. 724-730, 67(3), Wiley Periodicals, Inc.

\* cited by examiner

SYSTEMS AND METHODS FOR ACCELERATED MR THERMOMETRY

CROSS-REFERENCE TO RELATED APPLICATION

This application claims priority to and benefit under 35 U.S.C § 119(e) of U.S. Provisional Patent Application Ser. No. 61/974,234, entitled "Accelerating 3D Spiral MR Thermometry with the Kalman Filter," filed Apr. 2, 2014, which is hereby incorporated by reference in its entirety as if fully set forth below.

Some references, which may include patents, patent applications, and various publications, are cited in a reference list and discussed in the disclosure provided herein. The citation and/or discussion of such references is provided merely to clarify the description of the present disclosure and is not an admission that any such reference is "prior art" to any aspects of the present disclosure described herein. All references cited and discussed in this specification are incorporated herein by reference in their entireties and to the same extent as if each reference was individually incorporated by reference. In terms of notation, hereinafter, "[n]" may represent the $n^{th}$ reference cited in the reference list. For example, [5] represents the $5^{th}$ reference cited in the reference list, namely, Stafford, et al. MRM. 2000; 43:909-912.

STATEMENT REGARDING FEDERALLY SPONSORED RESEARCH

This invention was made with government support under grant HL079110, awarded by the National Institutes of Health. The government has certain rights in the invention.

BACKGROUND

MR-guided focused ultrasound (MRgFUS) is a promising non-invasive technique for cancer therapy, neural tissue ablation, and drug delivery across the blood brain barrier [1,2]. Real time MR thermometry of the heated volume, which can be based on the proton-resonance frequency (PRF) shift [3], can be an aspect of these procedures. Early work in the field focused on 2D imaging, either of one slice or a small number of slices; however, the desire to monitor the entire sonicated volume has led the field towards the development of rapid, 3D methods [4]. Acquiring fully sampled 3D volumetric data to measure phase changes due to the PRF shift in response to heating is time consuming, however, and so it is desirable to develop accelerated methods in order to meet the spatial and temporal requirements for adequate monitoring of thermal therapy.

The data acquisition efficiency of spiral trajectories can be higher than that of Cartesian scanning. Therefore, spiral trajectories are an attractive way in which to improve temporal resolution while maintaining spatial resolution in MR thermometry [5]. Additionally, spirals can have good robustness in the presence of motion and, for MRgFUS, off-resonance may not cause a shift in the position of the hot-spot as it does for EPI-based methods. Further speed-ups can be gained by utilizing the large amount of static spatial information present in the series of thermal maps. The Kalman filter method can use a statistical model improve a series of temporal images and has been successful in acceleration of myocardial imaging [6], and can provide real time feedback in MRI thermometry [7]. Accelerated thermometry with a 3D spiral acquisition and Kalman filter reconstruction may provide significant advantages.

It is with respect to these and other considerations that the various embodiments described below are presented.

SUMMARY

In one aspect, the present disclosure relates to a method for accelerated magnetic resonance thermometry is disclosed. In one exemplary embodiment, the method includes acquiring undersampled magnetic resonance data associated with an area of interest of a subject receiving focused ultrasound treatment. The method also includes reconstructing images corresponding to the area of interest based on the acquired magnetic resonance data, wherein the reconstructing includes using Kalman filtering.

The method may further include measuring phase changes from proton-resonance frequency (PRF) shift associated with heating in the area of interest caused by the focused ultrasound treatment. The method may further include, based on at least one of the measured phase changes and images generated from the reconstruction, determining one or more characteristics associated with a physiological activity in the area of interest. The acquiring can include spiral sampling. The acquiring using the spiral sampling can include using a three-dimensional interleaved stack-of-spirals spoiled gradient echo sequence.

In another aspect, the present disclosure relates to a system for accelerated magnetic resonance thermometry. In one exemplary embodiment, the system includes a data acquisition device configured to acquire undersampled magnetic resonance data associated with an area of interest of a subject receiving focused ultrasound treatment. The system also includes an image reconstruction device configured to reconstruct images corresponding to the area of interest based on the acquired magnetic resonance data, wherein the reconstructing may include using Kalman filtering.

The system may further include a phase change measurement device configured to measure phase changes from proton-resonance frequency (PRF) shift associated with heating in the area of interest caused at least in part by the focused ultrasound treatment. The system may include one or more processors configured to execute instructions to cause the system to, based on at least one of the measured phase changes and the images generated from the reconstruction, determine one or more characteristics associated with a physiological activity in the area of interest. The acquiring may include spiral sampling. The acquiring may include using a three-dimensional interleaved stack-of-spirals spoiled gradient echo sequence.

In another aspect, the present disclosure relates to a non-transitory computer-readable medium storing instructions that, when executed by one or more processors, cause a computer to perform functions that include acquiring undersampled magnetic resonance data associated with an area of interest of a subject receiving focused ultrasound treatment. The functions performed also include reconstructing images corresponding to the area of interest based on the acquired magnetic resonance data, wherein the reconstructing may include using Kalman filtering.

The functions may further include measuring phase changes from proton-resonance frequency (PRF) shift associated with the heating in the area of interest caused by the focused ultrasound treatment. The functions may include, based on at least one of the measured phase changes and images generated from the reconstruction, determining one or more characteristics associated with a physiological activity in the area of interest. The acquiring may include spiral sampling. The acquiring using the spiral sampling may include using a three-dimensional interleaved stack-of-spirals spoiled gradient echo sequence.

Other aspects and features according to the present disclosure will become apparent to those of ordinary skill in the art, upon reviewing the following detailed description in conjunction with the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Aspects of the present disclosure relate to accelerated magnetic resonance thermometry. Although example embodiments of the present disclosure are explained in detail, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise.

Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose.

It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Further, it is contemplated that one or more data acquisition or data collection steps of a method may include acquiring, collecting, receiving, or otherwise obtaining data. By way of example, data acquisition or collection may include acquiring data via a data acquisition device, receiving data from an on-site or off-site data acquisition device or from another data collection, storage, or processing device. Similarly, data acquisition or data collection devices of a system may include any device configured to acquire, collect, or otherwise obtain data, or to receive data from a data acquisition device within the system, an independent data acquisition device located on-site or off-site, or another data collection, storage, or processing device.

As discussed herein, a "subject" or "patient" may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g. rat, dog, pig, monkey), etc. It should be appreciated that the subject may be any applicable human patient, for example.

In the following description, references are made to the accompanying drawings that form a part hereof and that show, by way of illustration, specific embodiments or examples. In referring to the drawings, like numerals represent like elements throughout the several figures.

Figure 1:
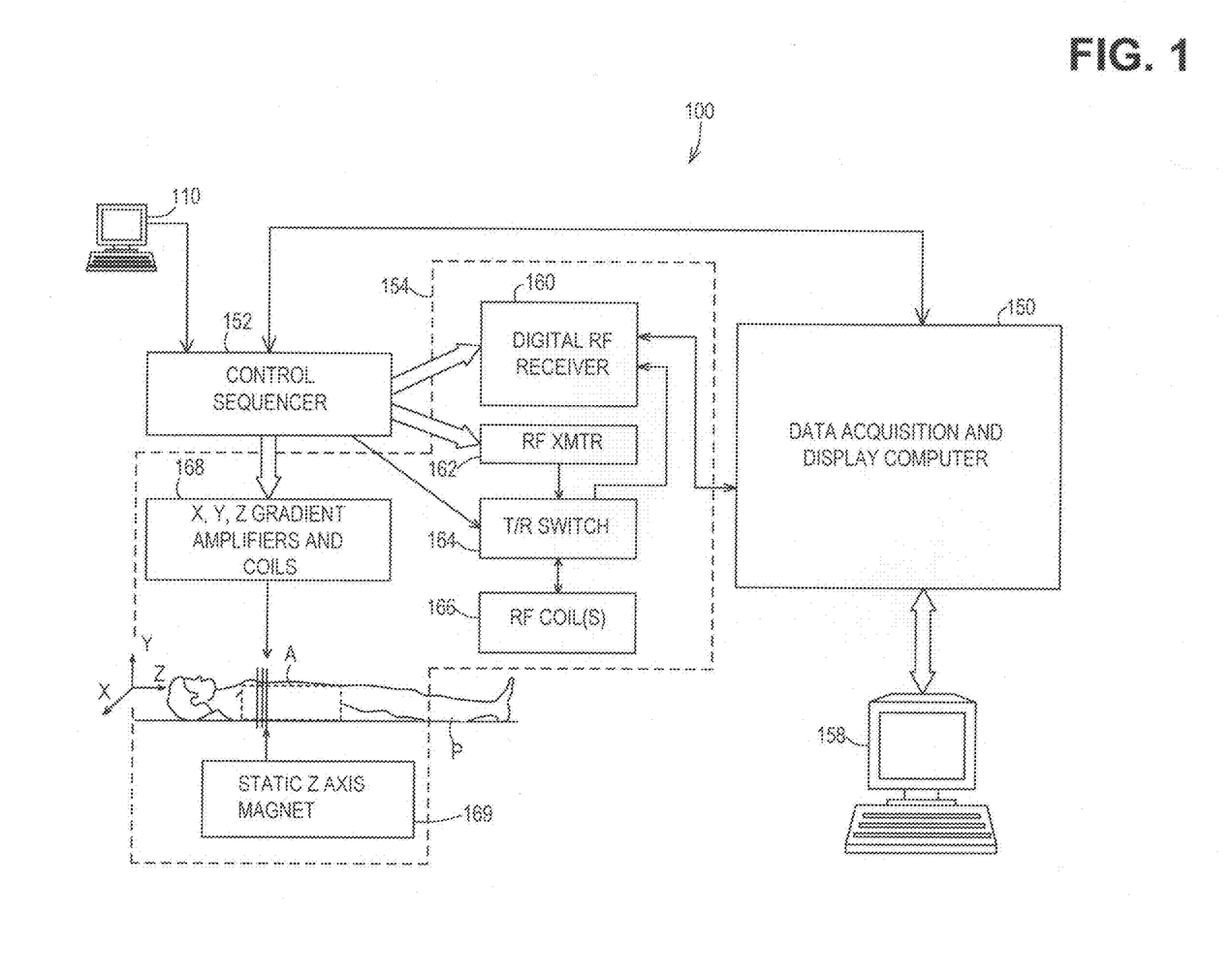
FIG. 1 is a system diagram illustrating an imaging system capable of implementing aspects of the present disclosure in accordance with one or more embodiments.

FIG. 1 is a system diagram illustrating an operating environment capable of implementing aspects of the present disclosure in accordance with one or more example embodiments. FIG. 1 illustrates an example of a magnetic resonance imaging (MRI) system 100, including a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest A corresponds to a region associated with one or more physiological activities in patient P. The area of interest shown in the example embodiment of FIG. 1 corresponds to a chest region of patient P, but the area of interest for purposes of implementing aspects of the disclosure presented herein is not limited to the chest area. It should be recognized and appreciated that the area of interest can be one or more of a brain region, cardiac region, and upper or lower limb regions of the patient P, for example. Physiological activities that may be analyzed by methods and systems in accordance with various embodiments of the present disclosure may include, but are not limited to, muscular movement, fluid flow, or various characteristics of biological tissue in particular areas of interest.

It should be appreciated that any number and type of computer-based medical imaging systems or components, including various types of commercially available medical imaging systems and components, may be used to practice certain aspects of the present disclosure. The scope of the disclosure is not intended to be specifically limited to magnetic resonance imaging (MRI) implementations or the particular system shown in FIG. 1.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 2:
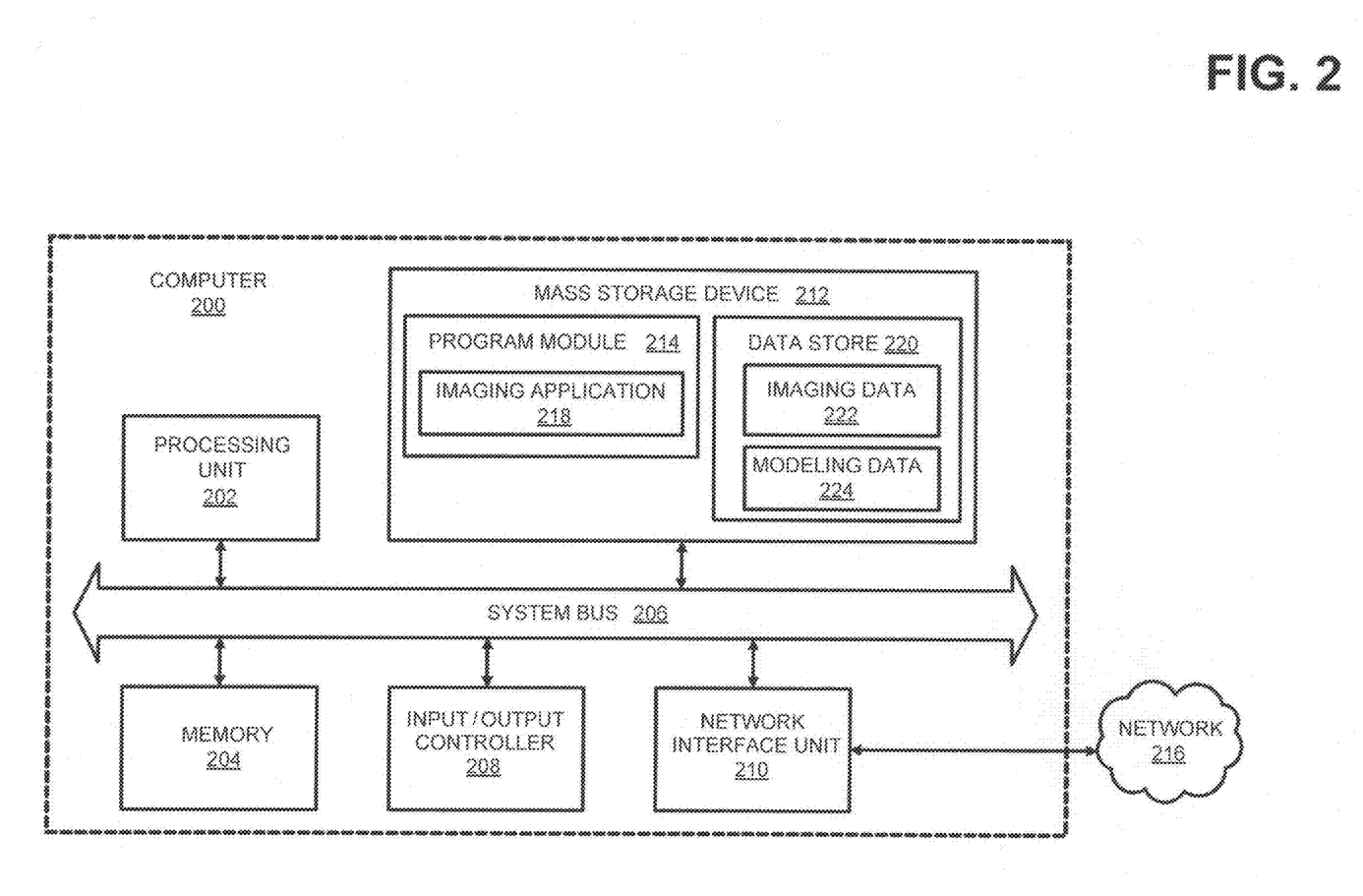
FIG. 2 is a computer architecture diagram showing a general computing system capable of implementing aspects of the present disclosure in accordance with one or more embodiments.

FIG. 2 is a computer architecture diagram showing a general computing system capable of implementing aspects of the present disclosure in accordance with one or more example embodiments described herein. A computer 200 may be configured to perform one or more functions associated with embodiments illustrated in FIG. 3. For example, the computer 200 may be configured to perform one or more of steps of a disclosed method for image reconstruction. It should be appreciated that the computer 200 may be implemented within a single computing device or a computing system formed with multiple connected computing devices. The computer 200 may be configured to perform various distributed computing tasks, which may distribute processing and/or storage resources among the multiple devices. The data acquisition and display computer 150 and/or operator console 110 of the system shown in FIG. 1 may include one or more systems and components of the computer 200.

As shown, the computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform one or more functions associated with embodiments illustrated in FIG. 3 discussed above. The program modules 214 may include an imaging application 218 for handling image data acquisition, receipt, and/or processing, or for directing an imaging device in communication with the computer to acquire and/or send image data. The computer 200 can include a data store 220 for storing data that may include imaging-related data 222 such as acquired image data, and a modeling data store 224 for storing image modeling data, or other various types of data utilized in practicing aspects of the present disclosure.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the computer 200.

By way of example, and not limitation, computer-storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, BLU-RAY, or other optical storage, magnetic cassettes, magnetic tape, magnetic disk storage or other magnetic storage devices, or any other medium which can be used to store the desired information and which can be accessed by the computer 200. Transitory signals are not "computer-storage media", "computer-readable storage medium" or "computer-readable storage media" as described herein.

According to various embodiments, the computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency network, a Bluetooth-enabled network, a Wi-Fi enabled network, a satellite-based network, or other wired and/or wireless networks for communication with external devices and/or systems. The computer 200 may also include an input/output controller 208 for receiving and processing input from a number of input devices. Input devices may include one or more of keyboards, mice, stylus, touchscreens, microphones, audio capturing devices, or image/video capturing devices. An end user may utilize such input devices to interact with a user interface, for example a graphical user interface, for managing various functions performed by the computer 200.

The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology. The computer-storage media may also represent secondary storage, whether implemented as hard drives or otherwise. Hard drive implementations may be characterized as solid state, or may include rotating media storing magnetically-encoded information. The program modules 214, which include the imaging application 218, include instructions that, when loaded into the processing unit 202 and executed, cause the computer 200 to provide functions associated with embodiments illustrated in FIG. 3. The program modules 214 may also provide various tools or techniques by which the computer 200 may participate within the overall systems or operating environments using the components, flows, and data structures discussed throughout this description.

In general, the program modules 214 may, when loaded into the processing unit 202 and executed, transform the processing unit 202 and the overall computer 200 from a general-purpose computing system into a special-purpose computing system. The processing unit 202 may be constructed from any number of transistors or other discrete circuit elements, which may individually or collectively assume any number of states. More specifically, the processing unit 202 may operate as a finite-state machine, in response to executable instructions contained within the program modules 214. These computer-executable instructions may transform the processing unit 202 by specifying how the processing unit 202 transitions between states, thereby transforming the transistors or other discrete hardware elements constituting the processing unit 202.

Encoding the program modules 214 may also transform the physical structure of the computer-storage media. The specific transformation of physical structure may depend on various factors, in different implementations of this description. Examples of such factors may include, but are not limited to the technology used to implement the computer-storage media, whether the computer storage media are characterized as primary or secondary storage, and the like. For example, if the computer-storage media are implemented as semiconductor-based memory, the program modules 214 may transform the physical state of the semiconductor memory, when the software is encoded therein. For example, the program modules 214 may transform the state of transistors, capacitors, or other discrete circuit elements constituting the semiconductor memory.

As another example, the computer-storage media may be implemented using magnetic or optical technology. In such implementations, the program modules 214 may transform the physical state of magnetic or optical media, when the software is encoded therein. These transformations may include altering the magnetic characteristics of particular locations within given magnetic media. These transformations may also include altering the physical features or characteristics of particular locations within given optical media, to change the optical characteristics of those locations. Other transformations of physical media are possible without departing from the scope of the present description, with the foregoing examples provided only to facilitate this discussion.

Figure 3:
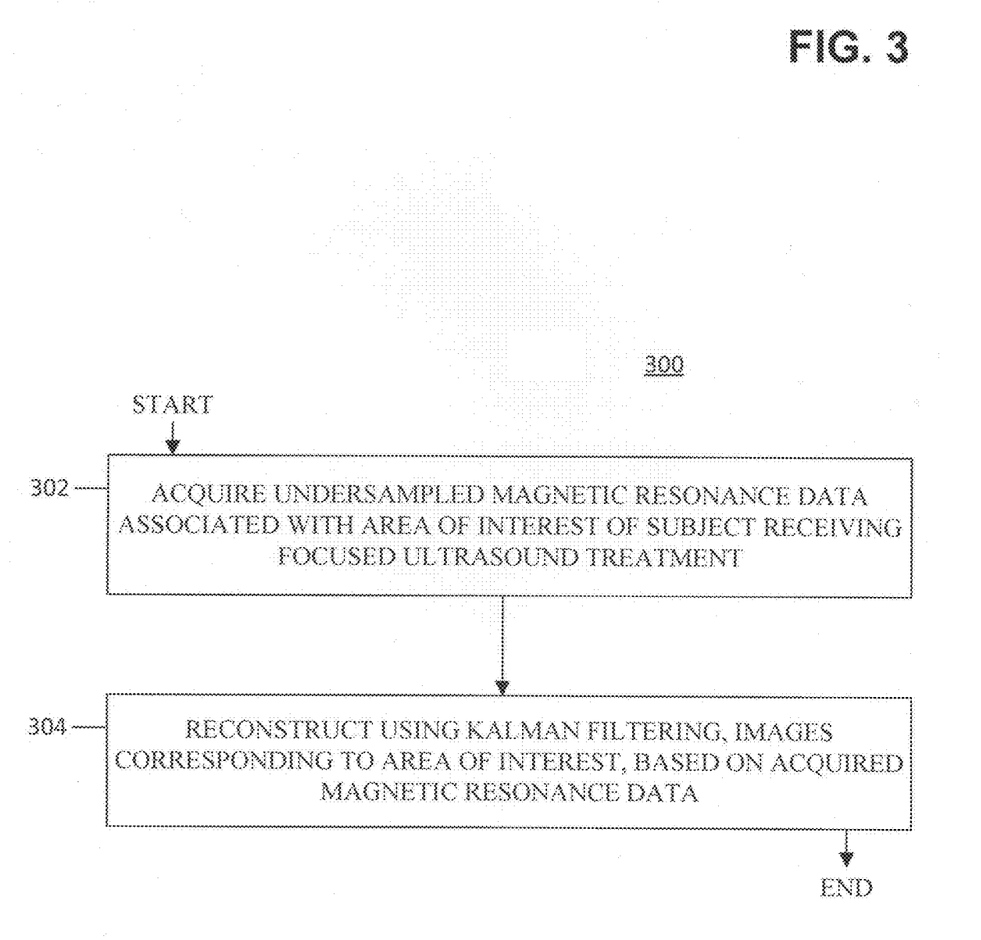
FIG. 3 is a flow diagram illustrating operations of a method for accelerated magnetic resonance thermometry in accordance with one embodiment.

FIG. 3 illustrates operational steps of a method 300 for accelerated magnetic resonance thermometry according to an exemplary embodiment of the present disclosure. The method 300 begins at block 302, where undersampled magnetic resonance data is acquired. The magnetic resonance data is associated with an area of interest of a subject that is receiving focused ultrasound treatment. The method 300 also includes, as shown at block 304, reconstructing images corresponding to the area of interest based on the acquired magnetic resonance data. The reconstructing includes using Kalman filtering.

In some embodiments, the method 300 may include the further step of measuring phase changes from proton-resonance frequency (PRF) shift associated with heating in the area of interest caused by the focused ultrasound treatment. In some embodiments, the method 300 may include the further step of, based on at least one of the measured phase changes and images generated from the reconstruction, determining one or more characteristics associated with a physiological activity in the area of interest. In some embodiments, the acquiring of block 302 may include spiral sampling. The acquiring using the spiral samples may include using a three-dimensional interleaved stack-of-spirals spoiled gradient echo sequence.

Example Implementations and Results

The following describes examples of implementing some aspects of the present disclosure, and corresponding results.

Methods

Figure 4:
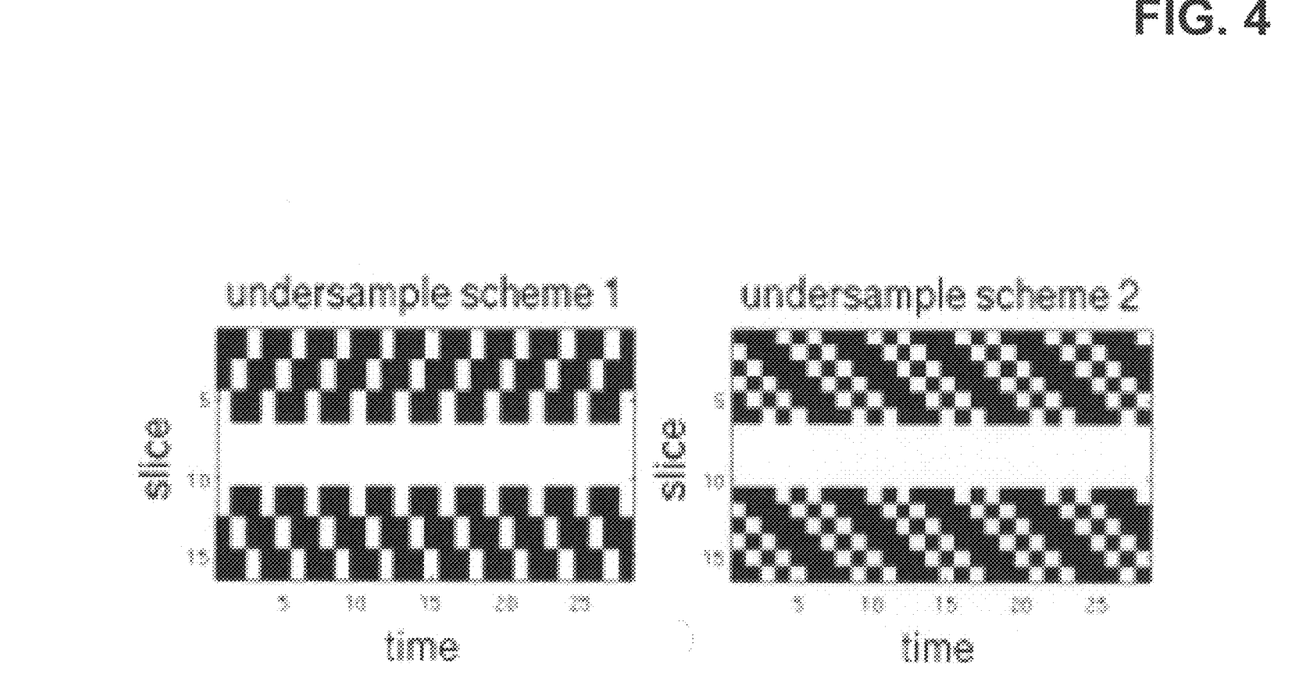
FIG. 4 is a representation of undersampling schemes in $k_z$-t space in accordance with one embodiment. White indicates acquired data.

The Kalman filter (KF) can be a recursive and efficient method to estimate the state of a process described by a dynamic state-space model:

$$x_k = f(x_{k-1})w_k$$

$$y_k = U_k F x_k + v_k$$

where, $x_k$ is the target image at the $k^{th}$ frame, $y_k$ is the corresponding acquired data, and $f(x_{k-1})$ is the state transition function. In the case of thermometry, $f(x_{k-1})$ is simply be $x_{k-1}$. F is a Fourier transform operator and $U_k$ is the undersampling scheme at acquisition k. w and v are the system and measurement noise. In some embodiments w and v can be assumed to have white Gaussian distributions with covariance matrices Q and R. In some embodiments, rapid imaging can be achieved by a 3D interleaved stack-of-spirals spoiled gradient echo sequence. The center of k-space can be fully sampled and provided low resolution images, which can be used as initial values and training data for the noise covariance matrix. FIG. 4 shows an embodiment of two undersampling schemes. In some embodiments, for image reconstruction, KF with ID Fourier transform can be performed in $k_{z-t}$ space for each acquired position along the spiral trajectory. According to some embodiments, each partition image can then be reconstructed by 2D gridding, and temperature maps can be calculated based on image phase differences from a reference frame.

In some embodiments, the accelerated 3D spiral trajectory and reconstruction were tested in a gel phantom, using an MR-compatible FUS system (RK-100, FUS Instruments Inc., Toronto) in a 3T whole-body scanner (Siemens Trio). In some embodiments, MRI parameters can be: FA=25°, TR/TE=15/6 ms, readout length=1 ms, interleaves=16 over a FOV of 64 mm$^2$ for an in-plane resolution of 2.7 mm$^2$ (zero-padded in reconstruction to 0.25 mm$^2$), 3D phase encodes=16 with through-plane resolution of 2 mm. In one embodiment, fully sampled data can be acquired by collecting all 3D phase encoding partitions per volume, for a total acquisition time per volume of 4.1 seconds. Rate 2 undersampled data can be acquired by skipping half of the 3D partitions per volume (as shown in FIG. 4), for a total acquisition time per volume of 2.05 seconds. The number of time points can be increased for the undersampled acquisition in order to match the total scanning time of the fully sampled dataset. In some embodiments, the in-plane (spiral) dimension may always be fully sampled.

In some embodiments, the MR pulse sequence can be run for 20 seconds to establish steady-state, continued running during a 20-second continuous sonication at 5 W to measure the focal temperature rise, then continued running for an additional 20 seconds. After repeating this procedure for each of the fully sampled and under sampled acquisitions, the temperature of the focal spot can be recorded and plotted for each by taking the mean of a 5×5 block of pixels centered on the focal spot in the slice with the maximum temperature response. In some embodiments, to monitor a remote location and evaluate the noise of the measurements, the mean and standard deviation of a 15×15 region can be recorded in a location remote from the focal spot.

Results

Figure 5:
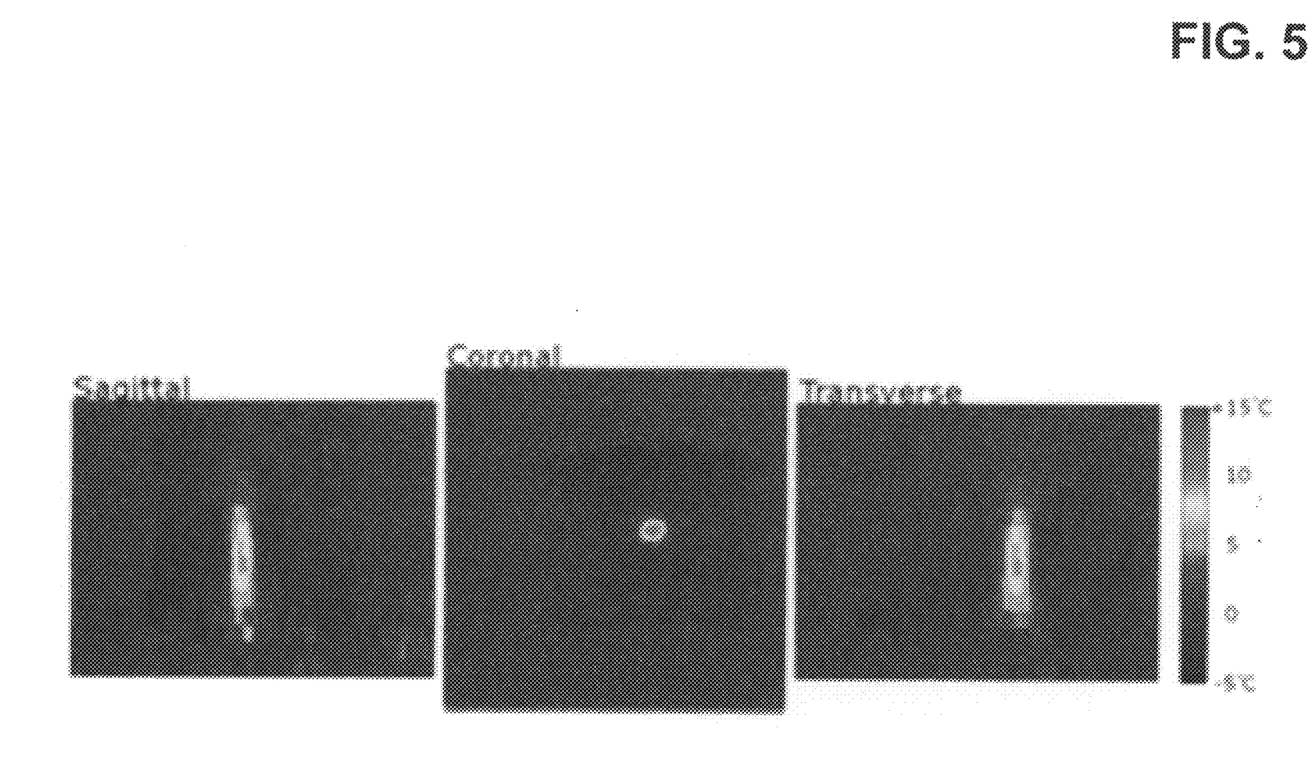
FIG. 5 is a 3D temperature map of phantom at t=40 seconds calculated from fully sampled data. The FUS focal spot is an ellipsoid with the long-axis oriented in the through-plane direction.
Figure 6:
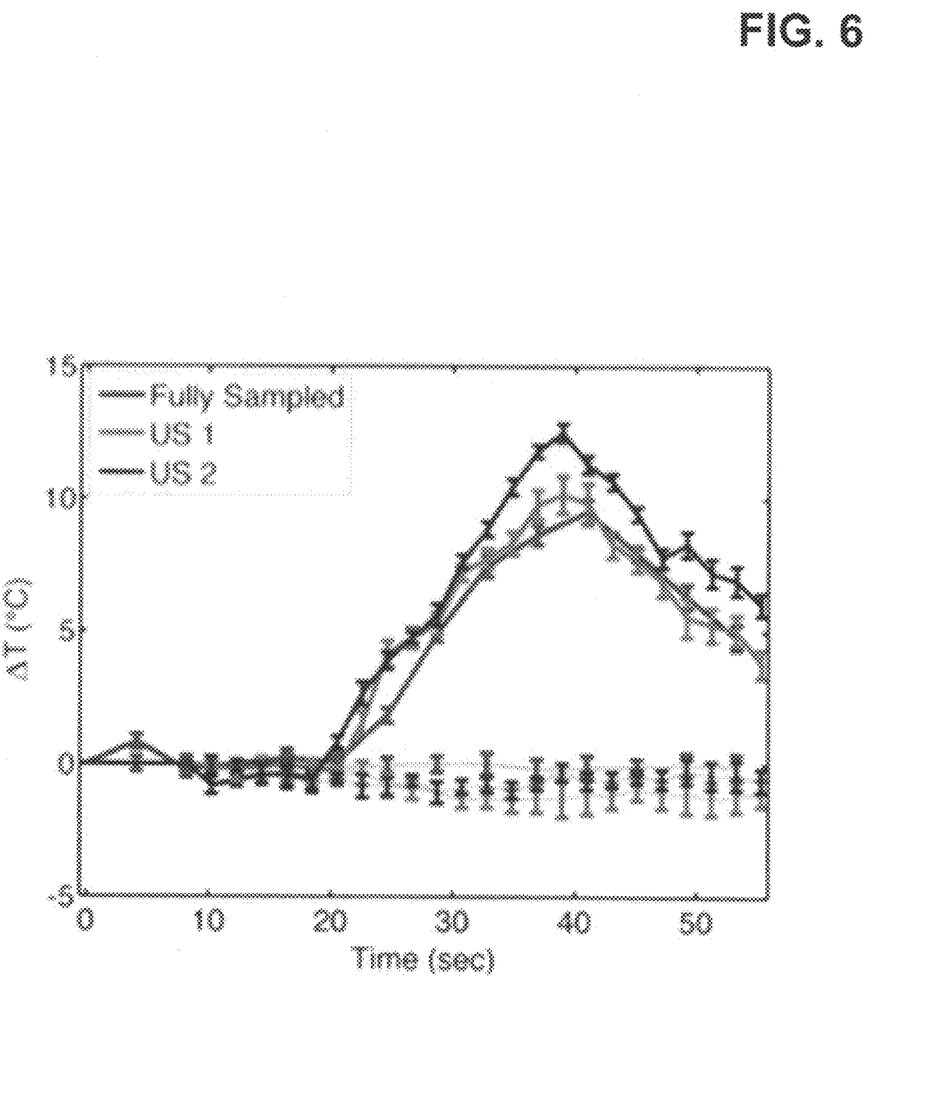
FIG. 6 is a graph showing measured temperature at ultrasound focal position (solid) and background (dotted) for fully sampled and undersampled acquisitions.

FIG. 5 shows sagittal, coronal (spiral plane), and transverse sections of an embodiment of a temperature map acquired from the fully-sampled data at the peak temperature time point. Background noise has been masked out of these images. In FIG. 6, the time-temperature plots of the FUS focal spots as well as a remote spot are shown. The measured temperatures follow predicted heating/cooling behavior for the experiment with small standard deviations (<0.5° C.). The differences between the curves can be at least partly explained by differing sonications. In some embodiments, the first 3 time points of the undersampled data can be thrown out because the Kalman filter requires several time points of data before reliable results are obtained.

Discussion

Spiral trajectories can allow faster imaging than Cartesian scanning [5], although the small size of the phantom and the large susceptibility gradients generated by the large pool of deionized water used in the FUS system can restrict the long readouts necessary to realize these advantages in this particular setup. Another advantage of spiral imaging is that while off-resonance can cause blurring, it may not shift the position of the focal spot, in contrast to EPI. With the short spiral readouts used, blurring was not significant. The use of the Kalman filter can facilitate a speed-up of 2× and can allow real-time feedback for accelerated MR thermometry.

CONCLUSION

The specific configurations, choice of materials and the size and shape of various elements can be varied according to particular design specifications or constraints requiring a system or method constructed according to the principles of the present disclosure. Such changes are intended to be embraced within the scope of the present disclosure. The presently disclosed embodiments, therefore, are considered in all respects to be illustrative and not restrictive. The scope of the present invention is indicated by the appended claims, rather than the foregoing description, and all changes that come within the meaning and range of equivalents thereof are intended to be embraced therein.

LIST OF REFERENCES

1. Kennedy, et al. Nat Rev Cancer. 2005; 5:321-327.
2. Medel, et al. Neurosurgery. 2012; 71:755-763.
3. Ishihara, et al. MRM. 1995; 34:814-823.
4. Todd, et al. MRM. 2012; 67:724-730.
5. Stafford, et al. MRM. 2000; 43:909-912.
6. Feng, et al. MRM 2012; 69:1346.
7. de Senneville, et al. ISMRM. 2012; 20:1558.

What is claimed is:

1. A method for accelerated magnetic resonance thermometry, comprising:
    acquiring, by applying a magnetic; resonance imaging sequence generated by a magnetic resonance imaging device, undersampled k-space magnetic resonance data associated with an area of interest of a subject receiving focused ultrasound treatment, wherein the magnetic resonance imaging sequence comprises a three-dimensional interleaved stack-of-spirals spoiled gradient echo sequence; and
    reconstructing images corresponding to the area of interest based on the acquired magnetic resonance data, wherein the reconstructing of the imams comprises:
    reconstructing the images from the undersampled k-space data using Kalman filtering,
    wherein the Kalman filtering comprises using a dynamic state-space model for the Kalman filtering,
    wherein the center of k-space is fully sampled and provides low resolution images used for initial values and training data for noise covariance for the Kalman filtering, and
    wherein the dynamic state-space model is according to:

$$x_k = f(x_{k-1}) + w_k$$

and $$y_k = U_x F x_k + v_k$$

wherein $x_k$ is target image at $k^{th}$ frame, $y_k$ is corresponding acquired data, $f(x_{k-1})$ is state transition function, F is Fourier transform operator, $U_k$ is undersampling scheme at acquisition k, and w and v are system and measurement noise.

2. The method of claim 1, further comprising:
    measuring phase changes from proton-resonance frequency (PRF) shift associated with heating in the area of interest caused by the focused ultrasound treatment.

3. The method of claim 2, further comprising:
    based on at least one of the measured phase changes and images generated from the reconstruction, determining one or more characteristics associated with a physiological activity in the area of interest.

4. The method of claim 1, wherein reconstructing the images includes reconstruction by 2D gridding.

5. A system for accelerated magnetic resonance thermometry, comprising,
    a magnetic resonance imaging device configured to apply a magnetic resonance imaging sequence configured to acquire undersampled k-space magnetic resonance data associated with an area at interest of a subject receiving focused ultrasound treatment, wherein the magnetic resonance imaging sequence comprises a three-dimensional interleaved stack-of-spirals spoiled gradient echo sequence; and
    an image reconstruction device configured to reconstruct images corresponding to the area at interest based on the acquired magnetic resonance data, wherein the reconstructing of the images comprises:
    reconstructing the images from the undersampled k-space data using Kalman filtering,
    wherein the Kalman filtering comprises using a dynamic state-space model for the Kalman filtering,
    wherein the center of k-space is fully sampled and provides low resolution images used for initial values and training data for noise covariance for the Kalman filtering, and
    wherein the dynamic; state-space model is according to:

$$x_k f(x_{k-1}) + w_k$$

and $$y_k = U_x F x_k + v_k$$

wherein $x_k$ is target image at $k^{th}$ frame, $y_k$ is corresponding acquired data, $f(x_{k-1})$ is state transition function, F is Fourier transform operator, $U_k$ is undersampling scheme at acquisition k, and w and v are system and measurement noise.

6. The system of claim 5, further comprising:
    a phase change measurement device configured to measure phase changes from proton-resonance frequency (PRF) shift associated with heating in the area of interest caused at least in part by the focused ultrasound treatment.

7. The system of claim 6, wherein the system further comprises:
one or more processors configured to execute instructions to cause the system to, based on at least one of the measured phase changes and the images generated from the reconstruction, determine one or more characteristics associated with a physiological activity in the area of interest.

8. The system of claim 5, wherein reconstructing the images includes reconstruction by 2D gridding.

9. A non-transitory computer-readable medium storing instructions that, when executed by one or more processors, cause a computing device to perform a method for accelerated magnetic resonance thermometry that comprises:
causing a magnetic resonance imaging device to apply a magnetic resonance imaging sequence configured to acquire undersampled k-space magnetic resonance data associated with an area of interest of a subject receiving focused ultrasound treatment, wherein the magnetic resonance imaging sequence comprises a three-dimensional interleaved stack-of-spirals spoiled gradient echo sequence; and
reconstructing images corresponding to the area of interest based on the acquired magnetic resonance data, wherein the reconstructing of the images comprises:
reconstructing the images from the undersampled k-space data using Kalman filtering,
wherein the Kalman filtering comprises using a dynamic state-space model for the filtering,
wherein the center of k-space is fully sampled and provides low resolution images used for initial values and training data for noise covariance for the Kalman filtering, and
wherein the dynamic state-space model s according to:

$$x_k = f(x_{k-1}) + w_k$$

and $$y_k = U_k F x_k + v_k$$

wherein $x_k$ is target image at $k^{th}$ frame, $y_k$ is corresponding acquired data, $f(x_{k-1})$ a state transition function, F a Fourier transform operator, $U_k$ is undersampling scheme at acquisition k and w and v are system and measurement noise.

10. The non-transitory computer-readable medium of claim 9, wherein the method further comprises:
measuring phase changes from proton-resonance frequency (PRF) shift associated with heating in the area of interest caused by the focused ultrasound treatment.

11. The non-transitory computer-readable medium of claim 10, wherein the method further comprises:
based on at least one of the measured phase changes and images generated from the reconstruction, determining one or more characteristics associated with a physiological activity in the area of interest.

12. The non-transitory computer-readable medium of claim 9, wherein reconstructing the images includes reconstruction by 2D gridding.

* * * * *